US011117330B2

(12) United States Patent
Weerakoon et al.

(10) Patent No.: US 11,117,330 B2
(45) Date of Patent: Sep. 14, 2021

(54) HOUSINGS FOR USE WITH INFLATION DEVICES AND RELATED METHODS

(71) Applicant: Merit Medical Systems, Inc., South Jordan, UT (US)

(72) Inventors: Prasad Weerakoon, Provo, UT (US); Jon Davis, Sandy, UT (US); Russell D. Heyborne, Riverton, UT (US); Larry T. Wilde, Hyrum, UT (US)

(73) Assignee: Merit Medical Systems, Inc., South Jordan, UT (US)

(*) Notice: Subject to any disclaimer, the term of this patent is extended or adjusted under 35 U.S.C. 154(b) by 288 days.

(21) Appl. No.: 15/202,834

(22) Filed: Jul. 6, 2016

(65) Prior Publication Data
US 2017/0007806 A1    Jan. 12, 2017

Related U.S. Application Data

(60) Provisional application No. 62/188,997, filed on Jul. 6, 2015.

(51) Int. Cl.
*B29C 65/58* (2006.01)
*A61M 25/10* (2013.01)

(52) U.S. Cl.
CPC ....... *B29C 65/58* (2013.01); *A61M 25/10182* (2013.11); *A61M 25/10188* (2013.11)

(58) Field of Classification Search
CPC .............. B29C 65/58; A61M 2209/04; A61M 2005/3142
See application file for complete search history.

(56) References Cited

U.S. PATENT DOCUMENTS

| 5,318,533 | A | 6/1994 | Adams et al. |
| 5,320,110 | A * | 6/1994 | Wang ................. A61B 10/0275 |
| | | | 600/566 |
| 6,139,523 | A | 10/2000 | Taylor et al. |
| 6,254,569 | B1 | 7/2001 | O'Donnell et al. |
| 2010/0005957 | A1 | 1/2010 | Ikari et al. |
| 2010/0114063 | A1 | 5/2010 | Recinella et al. |
| 2010/0217188 | A1 | 8/2010 | Lampropoulos et al. |
| 2013/0047395 | A1* | 2/2013 | Lampropolous ............................ |
| | | | A61M 25/10182 |
| | | | 29/407.01 |

(Continued)

FOREIGN PATENT DOCUMENTS

| JP | 53110188 | 9/1978 |
| JP | 06507085 | 11/1994 |
| JP | 2000313345 | 11/2000 |

OTHER PUBLICATIONS

International Search Report and Written Opinion dated Oct. 14, 2016 for PCT/US2016/041060.
European Search Report dated Jan. 30, 2019 for EP16821896.4.

*Primary Examiner* — Nathan R Price
*Assistant Examiner* — Weng Lee
(74) *Attorney, Agent, or Firm* — Stoel Rives LLP (57) ABSTRACT

A housing for use in connection with an inflation device can be coupled to a syringe body by a snap-fit connection. The snap-fit type mechanism can include an adaptor and a lock, such as a depressible lock. The housing can enclose an electrical circuit and a display screen that rests on a plurality of resilient pins. The circuit board may be held in place within the housing via one or more heat pins. The inflation device can be configured to measure pressure within a fluid reservoir of a syringe.

14 Claims, 12 Drawing Sheets

(56) References Cited

U.S. PATENT DOCUMENTS

2013/0338581 A1\* 12/2013 Stevens ........... A61M 25/10182
604/99.01

\* cited by examiner

HOUSINGS FOR USE WITH INFLATION DEVICES AND RELATED METHODS

RELATED APPLICATIONS

This application claims priority to U.S. Provisional Application No. 62/188,997, filed on Jul. 6, 2015 and titled, "Housings For Use With Inflation Devices and Related Methods" which is hereby incorporated by reference in its entirety.

TECHNICAL FIELD

The present disclosure relates generally to the field of medical devices. More particularly, some embodiments of the disclosure are directed to inflation devices that include a housing, along with related components and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which.

DETAILED DESCRIPTION

This disclosure broadly relates to syringe assemblies, inflation devices, inflation device components, and related methods for pressurizing, depressurizing, and/or otherwise displacing fluid. Certain embodiments relate, more particularly, to inflation devices in which a housing is coupled to a syringe via a snap-fit connection. Other or further embodiments relate to inflation devices that include a display screen that is supported by a plurality of resilient pins that deflect outward as the display screen is secured within a housing.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

The phrases "connected to" and "coupled to" are broad enough to refer to any suitable coupling or other form of interaction between two or more entities, including mechanical, fluid, and thermal interaction. Two components may be coupled to each other even though they are not in direct contact with each other. The phrases "attached to" or "attached directly to" refer to interaction between two or more entities which are in direct contact with each other and/or are separated from each other only by a fastener (e.g., adhesives, screws) of any suitable variety. The phrase "fluid communication" refers to arrangements in which a fluid (e.g., a gas or a liquid) can flow from one element to another element when the elements are in fluid communication with each other.

The term "heat pin" refers to an elongate structure that includes a first end for coupling to a housing and a second end that is configured to deform upon the application of heat.

The terms "proximal" and "distal" are opposite directional terms. For example, the distal end of a device or component is the end of the component that is furthest from the practitioner during ordinary use. The proximal end refers to the opposite end, or the end nearest the practitioner during ordinary use.

Figure 1:
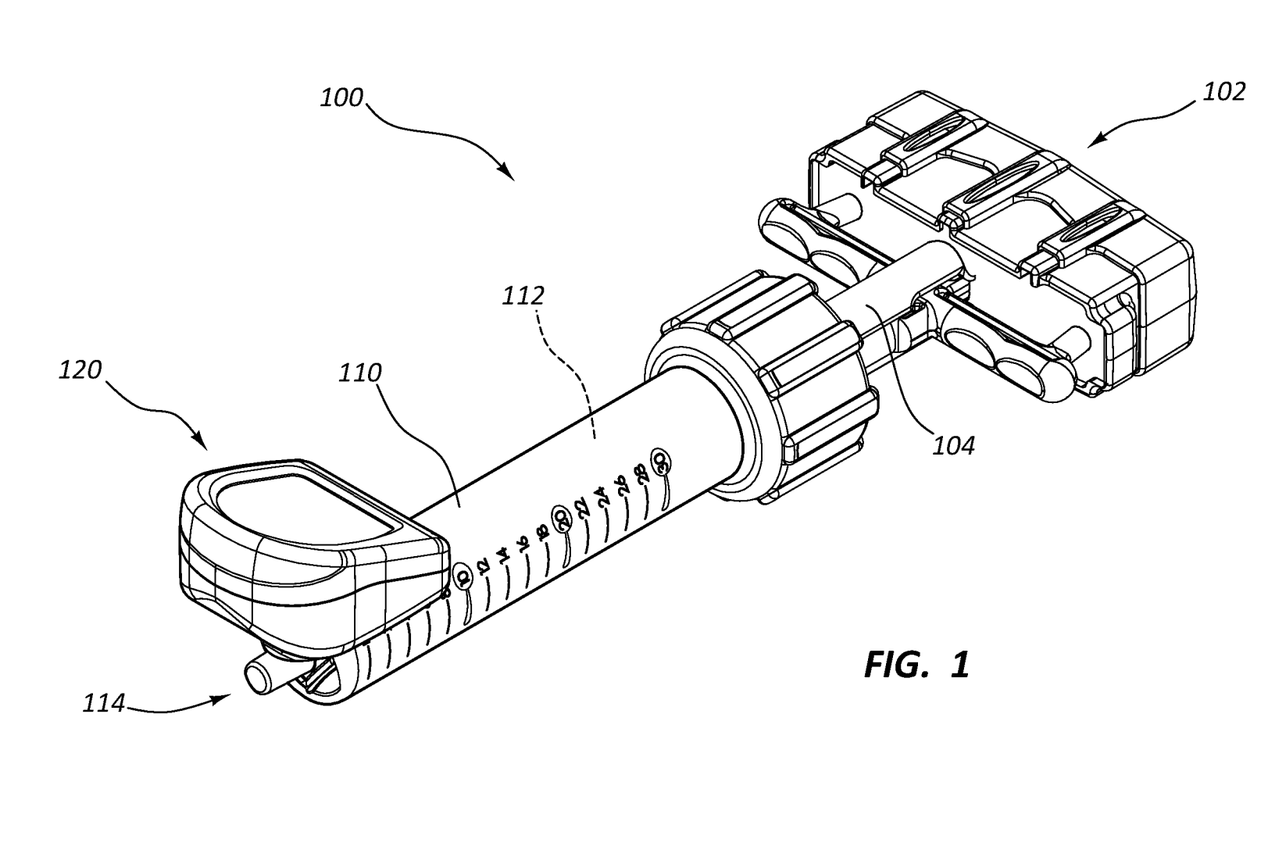
FIG. 1 is a perspective view of an inflation device.

FIGS. 1-7B provide alternative views of an inflation device 100 or portions thereof. For example, FIG. 1 provides a perspective view of the assembled inflation device 100. The inflation device 100 includes, among other elements, a handle 102, a plunger 104, a syringe body 110 (e.g., an elongate syringe barrel), and a housing 120. As depicted in FIG. 1, the handle 102 is coupled to the proximal end of the plunger 104. The plunger 104 may be configured to be disposed within the syringe body 110 such that advancement of the plunger 104 within the syringe body 110 causes displacement of fluid that is disposed within a fluid reservoir 112 of the syringe body 110. In some embodiments, the plunger 104 is configured to selectively couple to the syringe body 110 via a plurality of threads (not shown). In further embodiments, the handle 102 includes one or more elements that are designed to provide mechanical advantage in coupling and/or decoupling the plunger 104 to the syringe body 110.

The inflation device 100 may be used to inflate and/or pressurize a medical appliance or some other pressurizable element, such as an invertebral disc. For example, in some embodiments, the inflation device 100 may be used to inflate a medical appliance, such as a balloon catheter (not shown). More particularly, a distal port 114 of the syringe body 110 may be connected to a balloon catheter. When the plunger 104 is advanced within the syringe body 110, fluid may be forced from the fluid reservoir 112 of the syringe body 110 through the distal port 114 into the balloon catheter, thereby inflating the balloon of the balloon catheter. The inflation device 100 may be used in an analogous manner to inflate other medical appliances. In other instances, the inflation device 100 may be used to pressurize some other element, such as an invertebral disc in a lumbar provocative discography procedure.

As shown in FIG. 1, the inflation device 100 may also include a housing 120 that is configured to couple to the syringe body 110. The housing 120 may enclose or surround one or more components of the inflation device 100 to facilitate the measurement of pressure within the syringe body 110. Stated differently, the inflation device 100 may be used to measure pressure within the syringe body 110 during a medical procedure.

Figure 2:
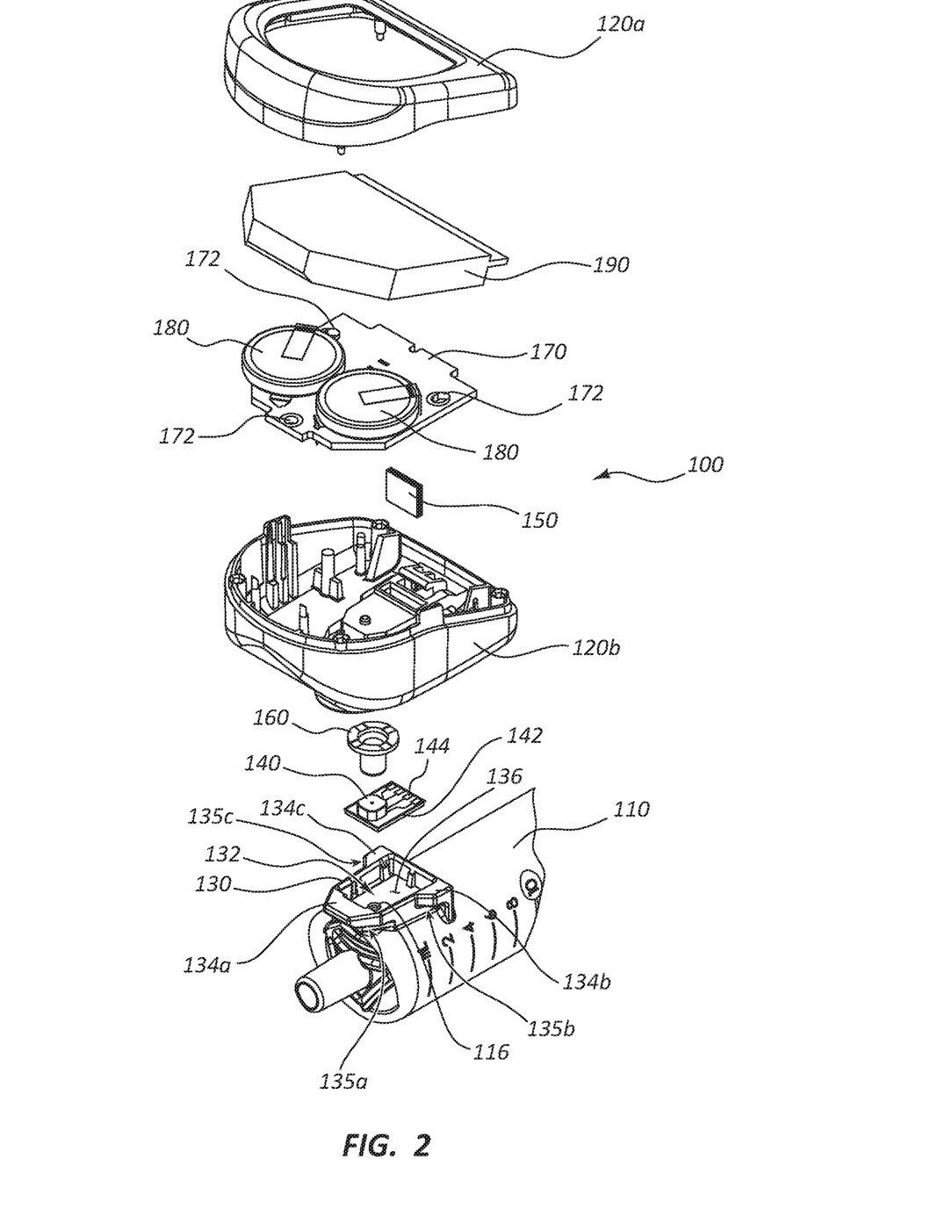
FIG. 2 is an exploded perspective view of a portion of the inflation device of FIG. 1.

FIG. 2 provides an exploded perspective view of a portion of the inflation device 100. More particularly, FIG. 2 shows, among other things, a distal region of the syringe body 110, an aperture 116 that extends through a wall of the syringe body 110, an adaptor 130 that is coupled to the syringe body 110, a lower portion of the housing 120b that is configured to couple to the syringe body 110 via the adaptor 130, a pressure transducer 140 that is coupled to a base plate 142, an elastomeric connector 150, an actuator 160, a circuit board 170 having a plurality of holes 172, a power source 180, a display screen 190, and an upper portion of the housing 120a. When assembled, the pressure transducer 140, the elastomeric connector 150, the circuit board 170, and the display screen 190 may be in electrical communication with one another.

As shown in FIG. 2, the aperture 116 and the adaptor 130 may be disposed adjacent a distal end of the syringe body 110. The adaptor 130 may be attached or otherwise coupled to the syringe body 110 in any suitable manner. For example, the adaptor 130 may be integrally formed with the syringe body 110, welded to the syringe body 110, or attached to the syringe body 110 via an adhesive.

In the depicted embodiment, the adaptor 130 includes a plurality of flanges 134a, 134b, 134c. For instance, the depicted embodiment includes a distal flange 134a that extends distal of a lower portion of the adaptor 130 and two proximal flanges 134b, 134c that extend lateral of the lower portion of the adaptor 130. Each of the flanges 134a, 134b, 134c includes a lower surface 135a, 135b, and 135c, respectively that is configured to contact an upper surface 121 of the lower portion of the housing 120b.

The adaptor 130 may include a cavity 132 having a bottom surface 136, the cavity 132 configured to receive both (1) the pressure transducer 140 and (2) the base plate 142 that is attached or otherwise coupled to the pressure transducer 140.

The pressure transducer 140 may be in fluid communication with the fluid reservoir 112 of the syringe body 110 when the inflation device 100 is fully assembled. Stated differently, fluid from the fluid reservoir 112 of the syringe body 110 may pass through a side wall of the syringe body 110 and through the base plate 142 such that the pressure transducer 140 is in fluid communication with the fluid reservoir 112 defined by the syringe body 110. In other words, in some embodiments, fluid may pass through an aperture 116 (or a group of apertures) that extend through both a wall of the syringe body 110 and the base plate 142. In some embodiments, a cross-section of the aperture 116 has a radius that is less than or equal to 0.8 mm, 0.6 mm, and/or 0.4 mm in length. The geometry of the aperture 116 may minimize or otherwise reduce the entry of air bubbles into the aperture 116. For example, the size, shape, and/or position of the aperture 116 relative to other components may minimize or prevent the entrapment of air therein. In some embodiments, a seal (not shown) may be disposed between the base plate 142 and the syringe body 110, thereby providing an airtight seal between the base plate 142 and the syringe body 110. Additionally of alternatively, the base plate 142 may be bonded to the syringe body 110 via an adhesive. The aperture 116 may include a radially enlarged portion adjacent the syringe body 110 such that that any excess adhesive used to bond the base plate 142 to the syringe body 110 flows into the enlarged portion rather than obstructing a central region of the aperture 116.

The base plate 142 may be made from any suitable material (e.g., fluid impermeable material). For example, in some embodiments, the base plate 142 includes a ceramic board and a plurality of electrical conduits that extend from the transducer 140 to a plurality of electrical contacts 144, such as those depicted adjacent the proximal end of the base plate 142 in FIG. 2. When in operation, the pressure transducer 140 may convert pressure into an analog electrical signal. The signal may then be relayed to the electrical contacts 144 via the electrical conduits.

Figure 3A:
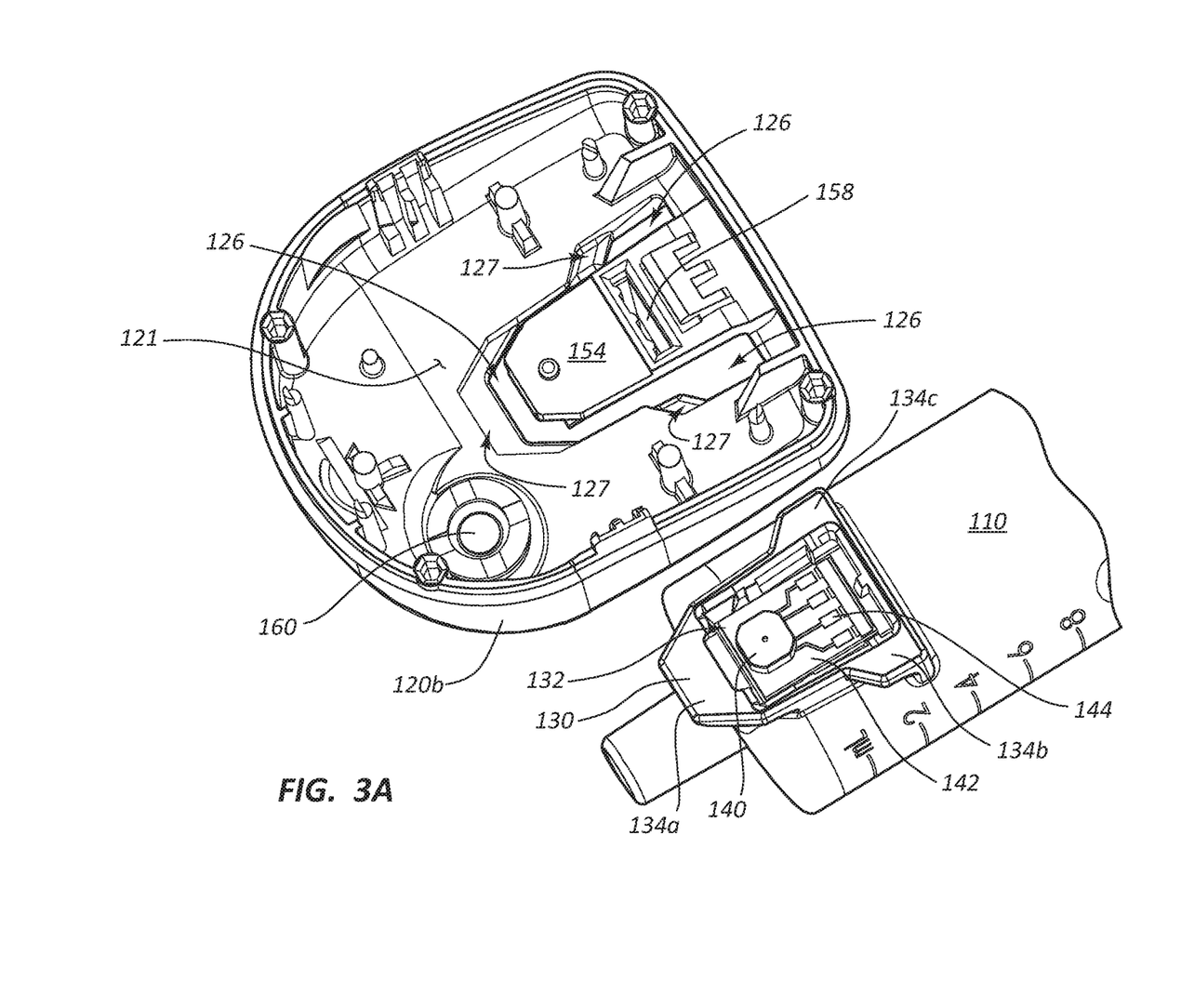
FIG. 3A is a perspective view of a portion of the inflation device of FIG. 1 in an unassembled configuration in which a syringe body is uncoupled from a lower portion of a housing.
Figure 3B:
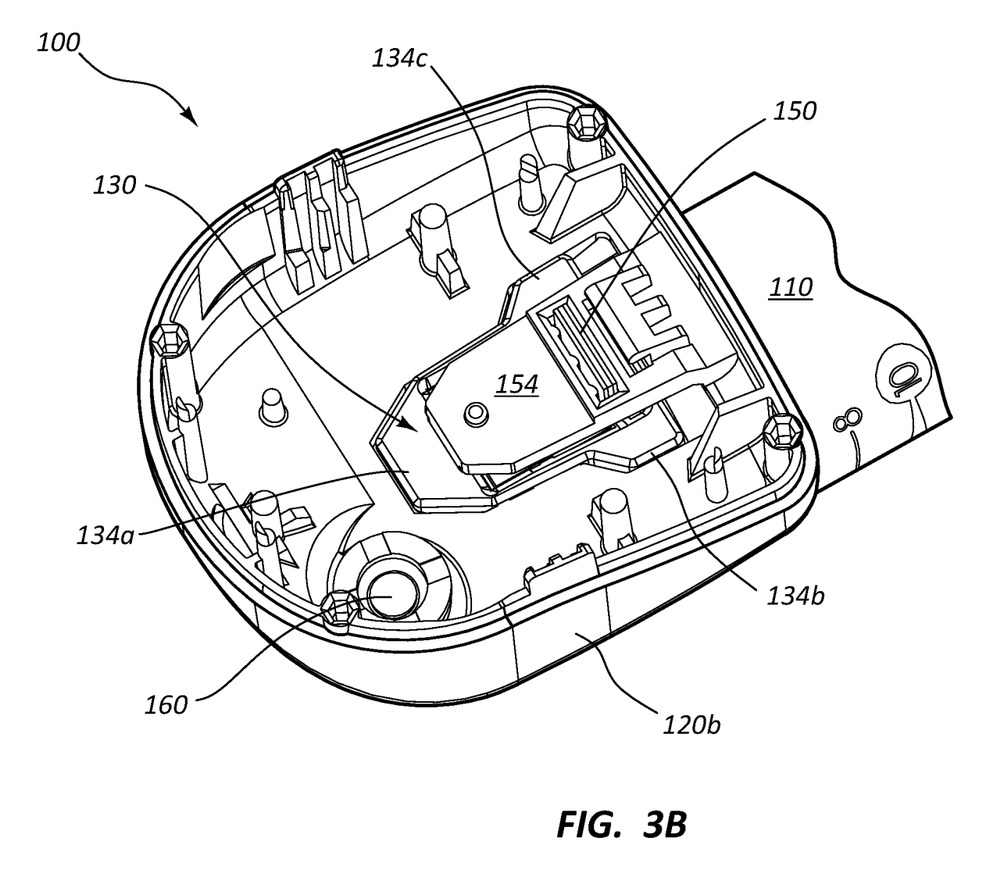
FIG. 3B is a perspective view of the portion of the inflation device depicted in FIG. 3A in a partially assembled configuration in which the syringe body is coupled to the lower portion of the housing.

FIG. 3A provides a perspective view of a portion of the inflation device 100 in a partially assembled configuration in which a syringe body 110 is uncoupled from a lower portion of the housing 120b. FIG. 3B provides a perspective view of the portion of the inflation device 100 depicted in FIG. 3A, with the syringe body 110 coupled to the lower portion of the housing 120b via an adaptor 130.

With reference to FIGS. 3A and 3B, the lower portion of the housing 120b may be configured to couple to the elongate syringe body 110 via a snap-fit connection that comprises an adaptor 130 and a lock 154. For instance, with the pressure transducer 140 and the base plate 142 disposed within the cavity 132 of the adaptor 130 as described with reference to FIG. 2, the adaptor 130 may be inserted through an opening 126 in the lower portion of the housing 120b and subsequently attached or otherwise coupled to the lower portion of the housing 120b. More particularly, the syringe body 110 and the adaptor 130 may initially be uncoupled from the lower portion of the housing 120b as shown in FIG. 3A. To insert the adaptor 130 into the lower portion of the housing 120b from the position depicted in FIG. 3A, the syringe body 110 and the adaptor 130 may be rotated along the longitudinal axis of the syringe body 110 such that a first proximal flange 134b is disposed higher than a second proximal flange 134c that is disposed opposite of the first proximal flange 134b. The first proximal flange 134b may then be inserted through the opening 126 of the lower portion of the housing 120b. Once the first proximal flange 134b has been inserted far enough into the opening 126 of the lower portion of the housing 120b, the syringe body 110 and the adaptor 130 may be rotated such that the second proximal flange 134c passes through the opening 126 as well. Once both proximal flanges 134b, 134c have passed through the opening 126, the adaptor 130 may rest on one or more surfaces of the lower portion of the housing 120b, (e.g., an angled surfaces 127) as shown in FIG. 3B. Stated differently, once the adaptor 130 has been inserted into the opening 126 of the lower portion of the housing 120b, the adaptor 130 may contact the lower portion of the housing 120b such that the lower surfaces 135a, 135b, and 135c of the plurality of flanges 134a, 134b, 134c are in contact with the upper surface 121 of the lower portion of the housing 120b.

In the depicted embodiment, a lock 154 is attached or otherwise coupled to the lower portion of the housing 120b. For example, in some embodiments, the lock 154 is integrally formed with the lower portion of the housing 120b. The locking mechanism for the lock 154 is discussed in greater detail below in connection with FIGS. 4A and 4B.

The lock 154 may include a slot 158 (see FIG. 3A) that is configured to receive an elastomeric connector 150 (see FIG. 3B). Stated differently, the elastomeric connector 150 may extend through a lock 154 via the slot 158. The elastomeric connector 150 may be configured to electrically couple the pressure transducer 140 to a circuit board 170 (see e.g., FIG. 2). Stated differently, the elastomeric connector 150 may establish an electrical connection with both (1) the electrical contacts 144 of the base plate 142 and (2) the circuit board 170. In some embodiments, the elastomeric connector 150 may include compressible material, such as silicone rubber. Such material may allow the elastomeric connector 150 to be compressed when squeezed by opposing forces provided by the base plate 142 and the circuit board 170.

In some embodiments, the elastomeric connector 150 includes a plurality of vertically oriented layers. The layers may be arranged in an alternating pattern, with conductive layers adjacent to non-conductive layers. An electrical signal that is relayed to the electrical contacts 144 of the base plate 142 from the pressure transducer 140 may be conveyed to the circuit board 170 via the one or more conductive layers of the elastomeric connector 150. In this manner, a solderless electrical connection between the pressure transducer 140 and the circuit board 170 may be established.

Figure 4A:
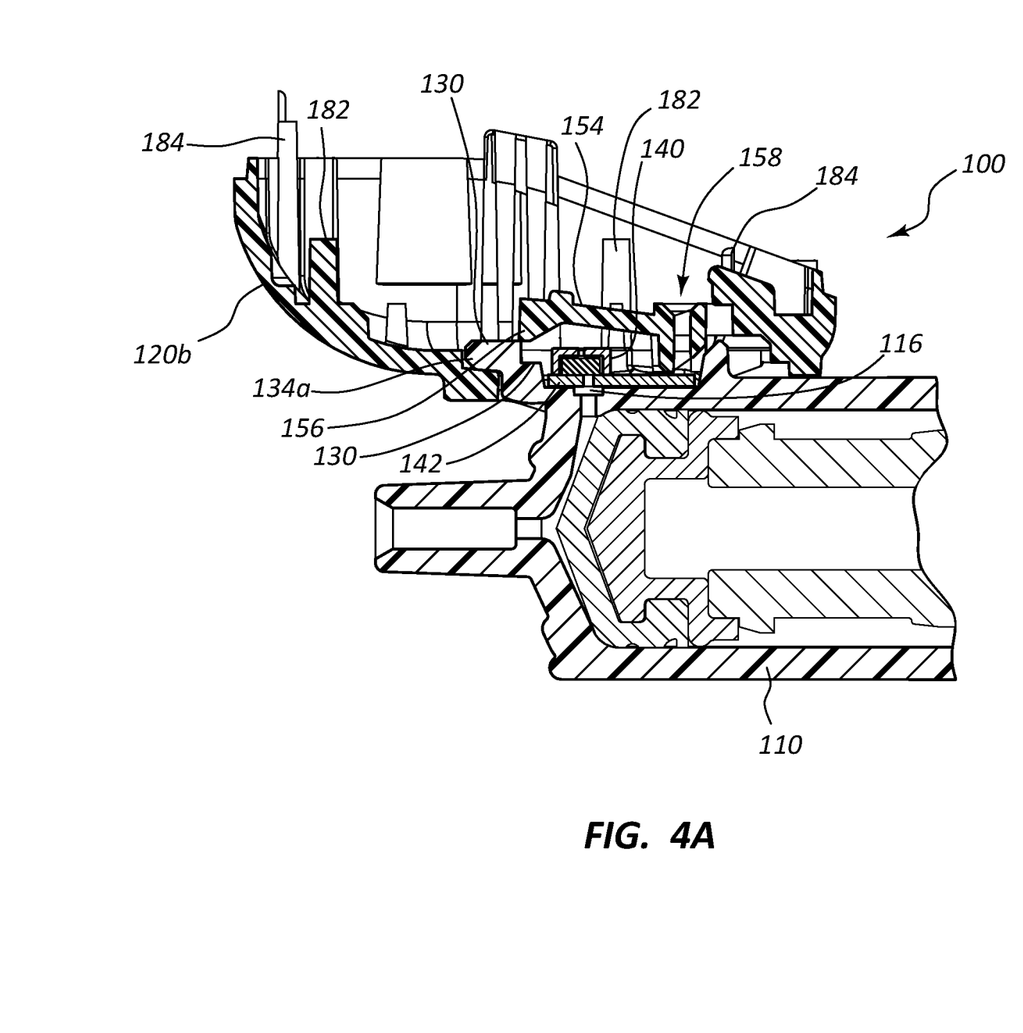
FIG. 4A is a cross-sectional view of a portion of the inflation device of FIG. 1 in an unlocked and partially assembled configuration.
Figure 4B:
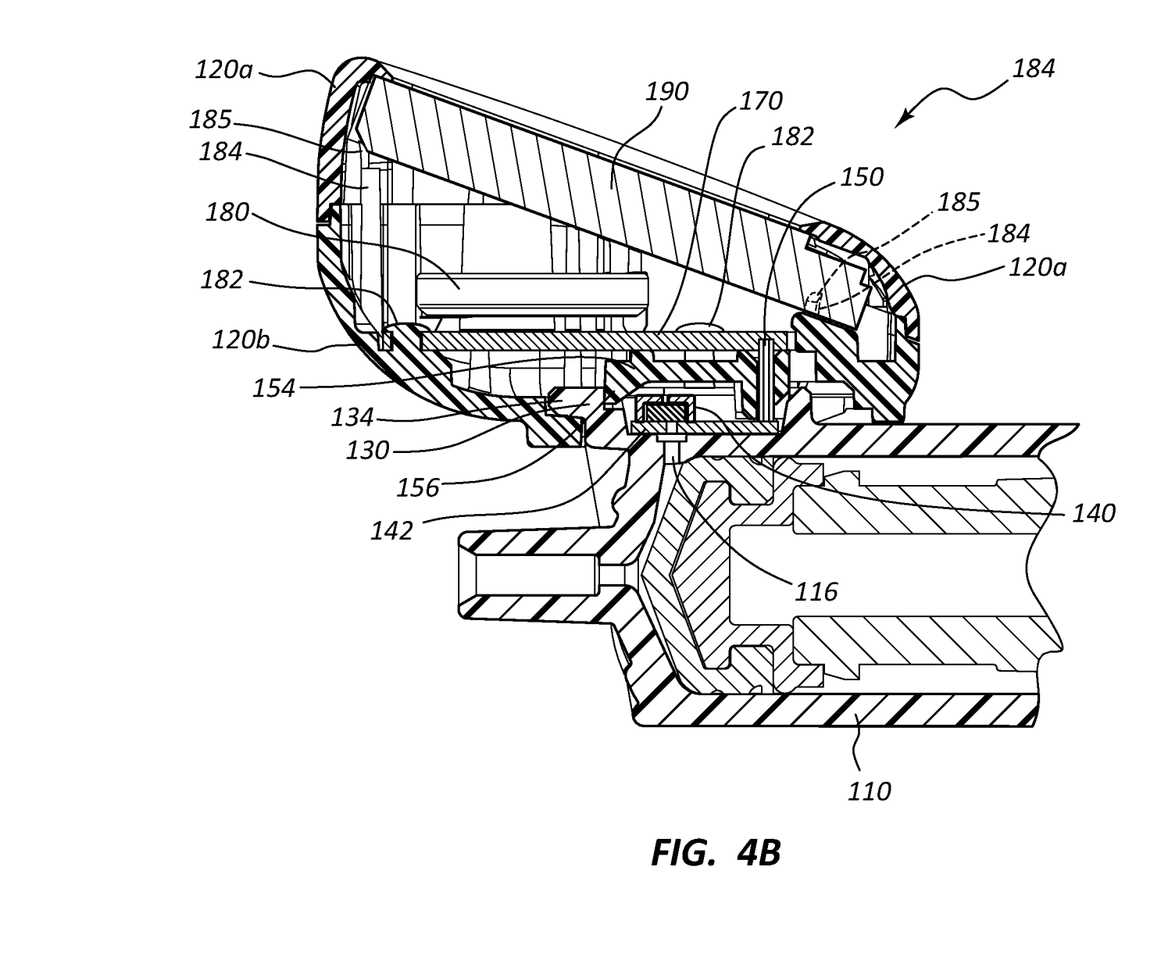
FIG. 4B is a cross-sectional view of a portion of the inflation device of FIG. 1 in a locked and assembled configuration.

FIGS. 4A and 4B provide cross-sectional views of a portion of the inflation device 100. More particularly, FIG. 4A provides a cross-sectional view of the inflation device 100 in a partially assembled and unlocked configuration, while FIG. 4B depicts the inflation device 100 in an assembled and locked configuration.

With reference to FIG. 4A, the adaptor 130 may exert an upward force on a lock 154 that is coupled to the lower portion of the housing 120b as the adaptor 130 is inserted through the opening of the lower portion of the housing 120b as described above in connection with FIGS. 3A and 3B. For example, as depicted in FIG. 4A, as the adaptor 130 is inserted into the lower portion of the housing 120b, the distal portion of the lock 154 may be deflected in an upward direction.

The lock 154 may include a first (e.g., proximal) portion for coupling to the lower portion of the housing 120b, and a second (e.g., distal) portion that is configured to deflect upward as the adaptor 130 is inserted into the opening of the lower portion of the housing 120b. The second portion of the lock 154 may also include a downward protrusion 156 that is configured to engage with the adaptor 130 to prevent movement of the adaptor 130 relative to the lower portion of the housing 120b. Stated differently, once the adaptor 130 has been inserted through the opening such that the lower surfaces 135a, 135b, and 135c of the plurality of flanges (e.g., flange 134a) are in contact with the lower portion of the housing 120b, a downward force applied to the distal portion of the lock 154 may cause the downward protrusion 156 of the lock 154 to engage with the adaptor 130 as shown in FIG. 4B, thereby restricting movement of the adaptor 130 relative to the lower portion of the housing 120b. The downward force may be externally applied (e.g., the distal portion of the lock 154 may be manually depressed) or result from the bias of the lock 154 to be disposed as shown in FIG. 4B. As described in further detail below in connection with FIGS. 6A and 6B, a circuit board 170 may be placed over the lock 154 to hold the lock 154 in a position such that the downward protrusion 156 is engaged with the adaptor 130 as shown in FIG. 4B. In this manner, the adaptor 130 may be locked in place relative to the lower portion of the housing 120b via a lock 154 that is coupled to the lower portion of the housing 120b.

FIGS. 4A and 4B also depict other components of the inflation device 100 that are described in further detail in connection with other figures, such as the upper portion of the housing 120a, the display screen 190, the resilient pins 184, the heat pins 182, the power source 180, the elastomeric connector 150, the pressure transducer 140, the base plate 142, and the syringe body 110. FIG. 4B shows that the pressure transducer 140 and the base plate 142 for the pressure transducer 140 may be disposed between the adaptor 130 and the lock 154 when the inflation device 100 is in an assembled configuration.

Figure 5A:
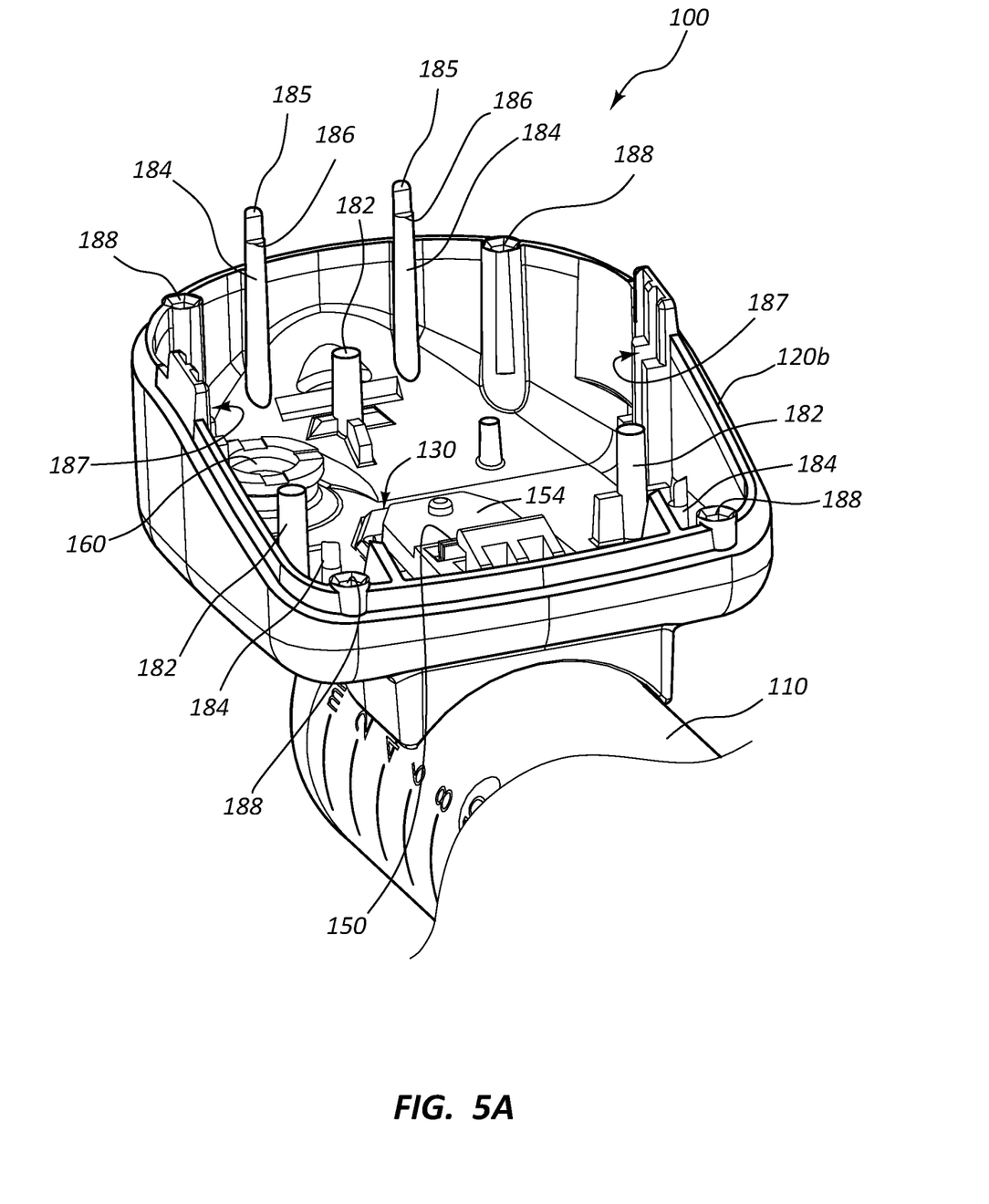
FIG. 5A is a perspective view of a portion of the inflation device of FIG. 1 in a partially assembled configuration.
Figure 5B:
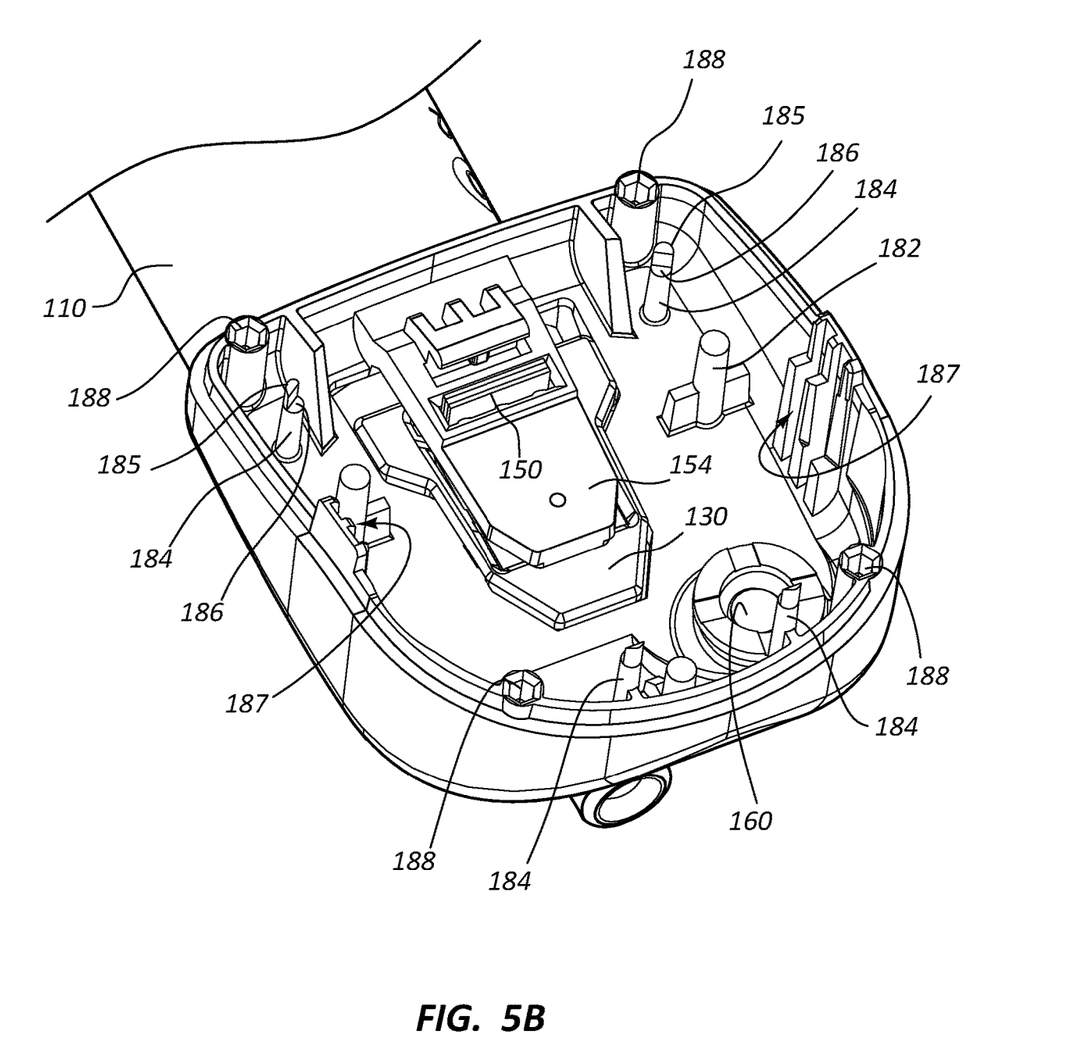
FIG. 5B is another perspective view of a portion of the inflation device of FIG. 1 in the partially assembled configuration of FIG. 5A.

FIGS. 5A and 5B provide alternative perspective views of a distal end of the inflation device 100 in a partially assembled configuration (e.g., prior to placement of a circuit board 170). The illustrations provided in FIGS. 5A and 5B show various inflation device components, such as the syringe body 110, the lower portion of the housing 120b, the adaptor 130, the elastomeric connector 150, and the lock 154 that have been described above in connection with other figures.

FIGS. 5A and 5B also depict various other elements of the inflation device 100. For example, the depicted embodiment includes a plurality of heat pins 182, a plurality of resilient pins 184, a plurality of side supports 187, a plurality of coupling elements 188, and an actuator 160.

In the depicted embodiment, each heat pin 182 includes an elongate shaft that has a first end for coupling to a lower portion of the housing 120b and a second end that is configured to deform (i.e., change shape) upon the application of heat. The heat pins 182 may extend in a substantially vertical direction from the base of the lower portion of the housing 120b. In the depicted embodiments, the heat pins 182 also include one or more shoulders that extend laterally from the elongate shaft. The shoulders may be configured to support a circuit board.

Each resilient pin 184 of the plurality of resilient pins 184 may extend in a generally upward direction from the base of the lower portion of the housing 120b. The resilient pins 184 may be generally elongate in shape. In some embodiments, the resilient pins 184 include a top portion that is shaped to support a display screen 190 (see FIGS. 4B, 7A, and 7B). For example, in the depicted embodiment, the top portion includes an angled portion 185 and a ledge 186. The resilient pins 184 may be formed from or comprise material that is capable of deflection, such as polycarbonate or other plastic materials.

With reference to FIG. 4B, the resilient pins 184 may be configured to deflect outward when supporting a display screen 190. In other words, as a downward force is applied to the display screen 190 by the upper portion of the housing 120a, the resilient pins 184 may deflect outward. Such deflection may be due, at least in part, to the shape, structure, thickness, and/or geometry of the resilient pin 184. For example, a relatively thin angled portion 185 of a resilient pin 184 may deflect outward while the remainder the of resilient pin 184 is not deflected (or deflected to a lesser extent than the angled portion 185).

With reference to FIGS. 5A and 5B, the plurality of coupling elements 188 may be configured for coupling a lower portion of the housing 120b to an upper portion of the housing. In some embodiments, the coupling elements 188 of the lower portion of the housing 120b are configured to couple to coupling elements of the upper portion of the housing via a snap-fit connection.

The plurality of side supports 187 may include a ledge that is configured to support a display screen. In some embodiments, the side supports 187 extend from one or more sides of the lower portion of the housing 120b.

The actuator 160 may be configured to power-up the inflation device 100. Stated differently, the actuator 160 may be used to toggle the inflation device 100 between a disabled state and an enabled state. In other or further embodiments, the actuator 160 may be configured to communicate with the circuit board 170 and the display screen 190 such that manipulation of the actuator causes the display screen 190 to transition between different visual displays. In the depicted embodiment, the practitioner may press upward on a button located on the underside of the lower portion of the housing 120b to manipulate the actuator 160.

Figure 6A:
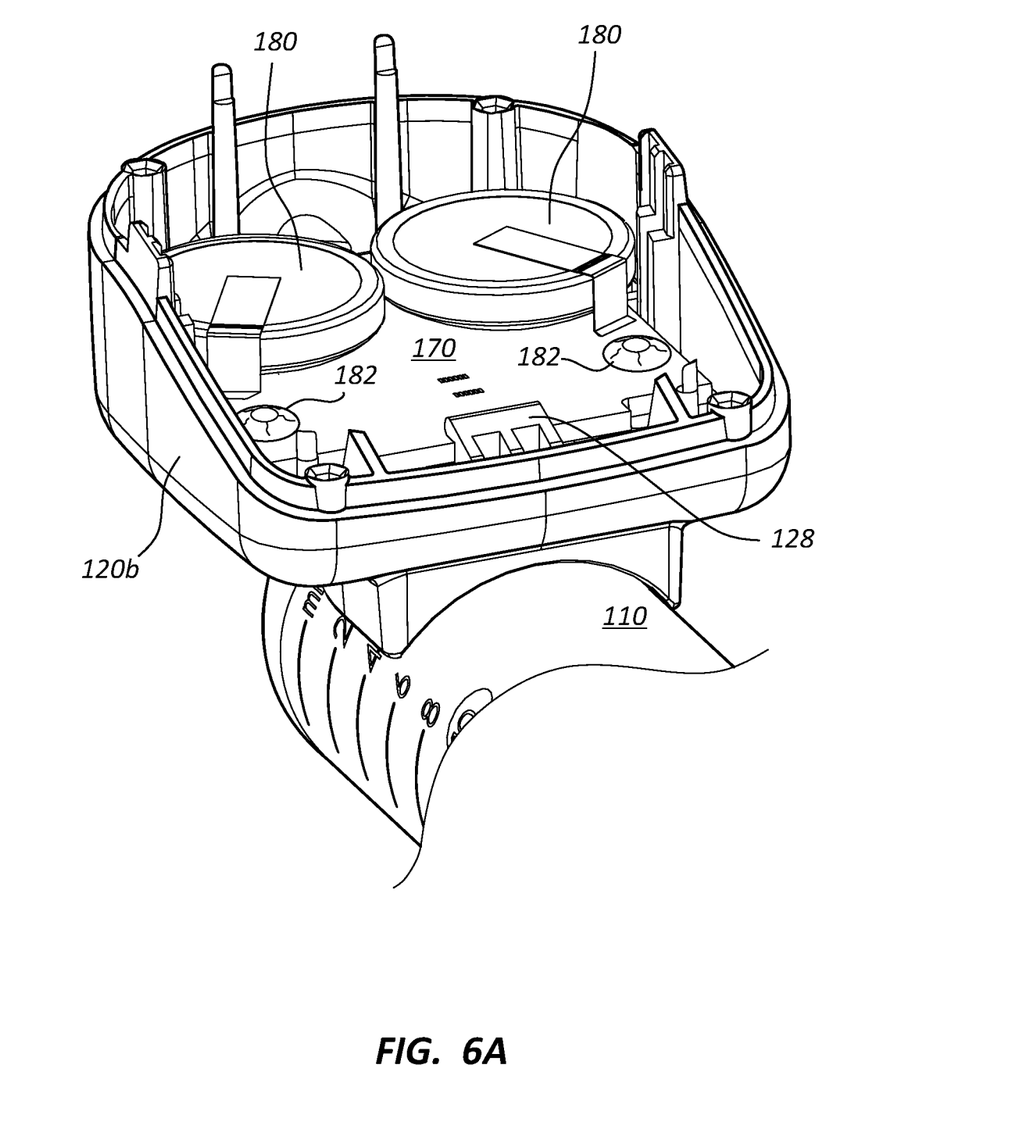
FIG. 6A is a perspective view of a portion of the inflation device of FIG. 1 in another partially assembled configuration.
Figure 6B:
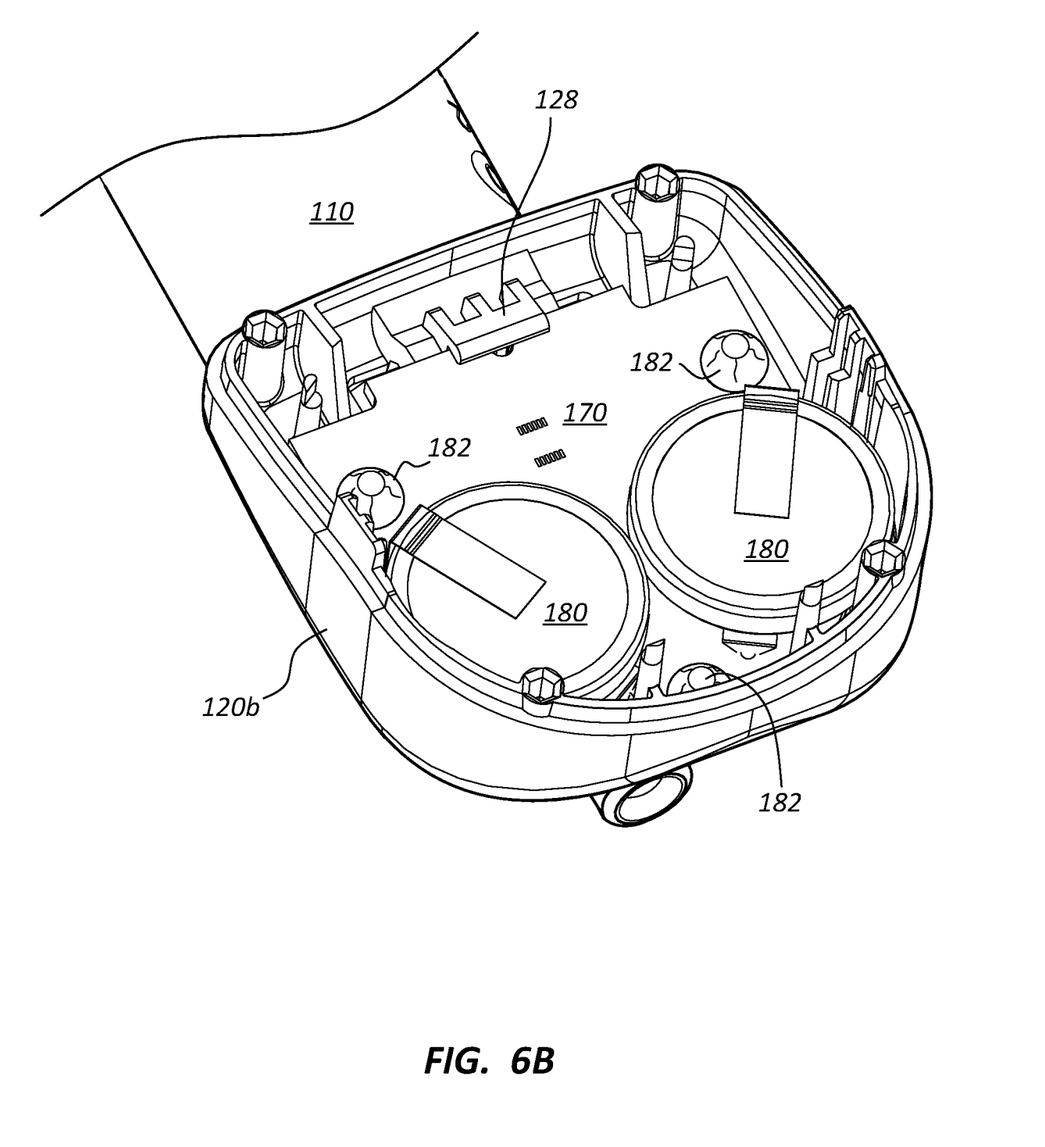
FIG. 6B is another perspective view of a portion of the inflation device of FIG. 1 in the partially assembled configuration of FIG. 6A.

FIGS. 6A and 6B provide alternative perspective views of a distal end of the inflation device 100 in a partially assembled configuration. More particularly, these figures depict a circuit board 170 that is coupled to the lower portion of the housing 120b.

The circuit board 170 may include circuitry and a plurality of holes 172 (the holes 172 are shown in FIG. 2). The circuitry may include logic to facilitate the conversion of a signal from the pressure transducer into a readout that is representative of the pressure within the fluid reservoir 112 of the syringe body 110. In the depicted embodiment, the circuit board 170 is placed over the heat pins 182 such that the circuit board 170 rests on one or more shoulders of the heat pins 182. Stated differently, the circuit board 170 may be placed by aligning the plurality of holes 172 of the circuit board 170 with the heat pins 182 such that the top portions of the heat pins 182 extend through the holes 172 of the circuit board 170. Then heat may be applied to the top portions of the heat pins 182, causing deformation of the heat pins 182. For example, the heat pins 182 may melt to form a mushroom-shaped head as depicted in FIGS. 6A and 6B. Such deformation may prevent uncoupling of the circuit board 170 from the heat pins 182. In this manner, the circuit board 170 may be fixedly coupled to the lower portion of the housing 120b.

The circuit board 170 may be further held in place by a circuit board engagement member 128 that extends upward from the lock 154. The circuit board engagement member 128 may be configured to interact with the circuit board 170 such that the circuit board 170 is placed at the proper location relative to the bottom portion of the housing 120b. For example, the circuit board engagement member 128—together with the heat pins 182—may be configured to ensure that the circuit board 170 is properly positioned to electrically couple to the elastomeric connector 150.

Figure 7A:
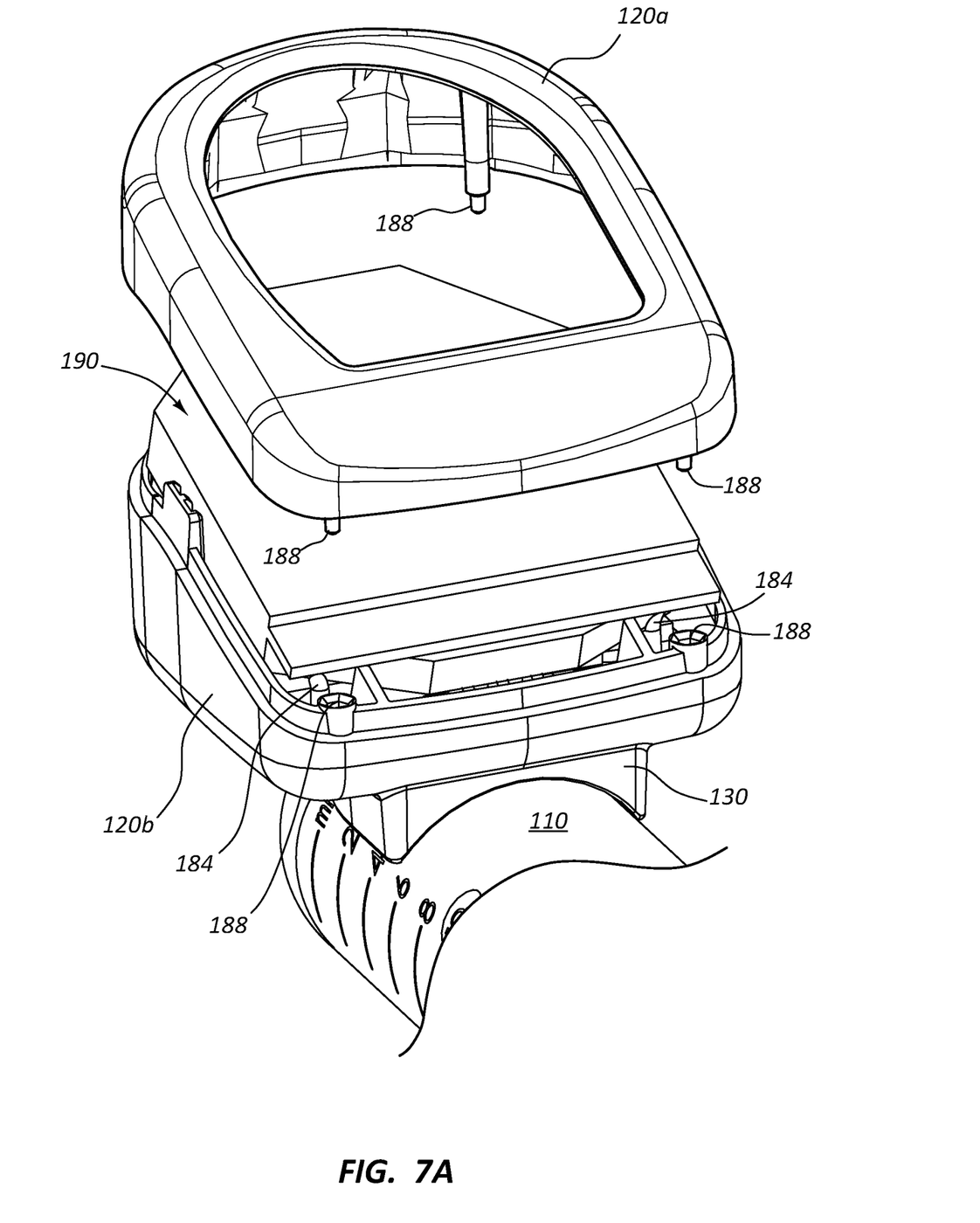
FIG. 7A is a perspective view of a portion of the inflation device of FIG. 1 in another partially assembled configuration.
Figure 7B:
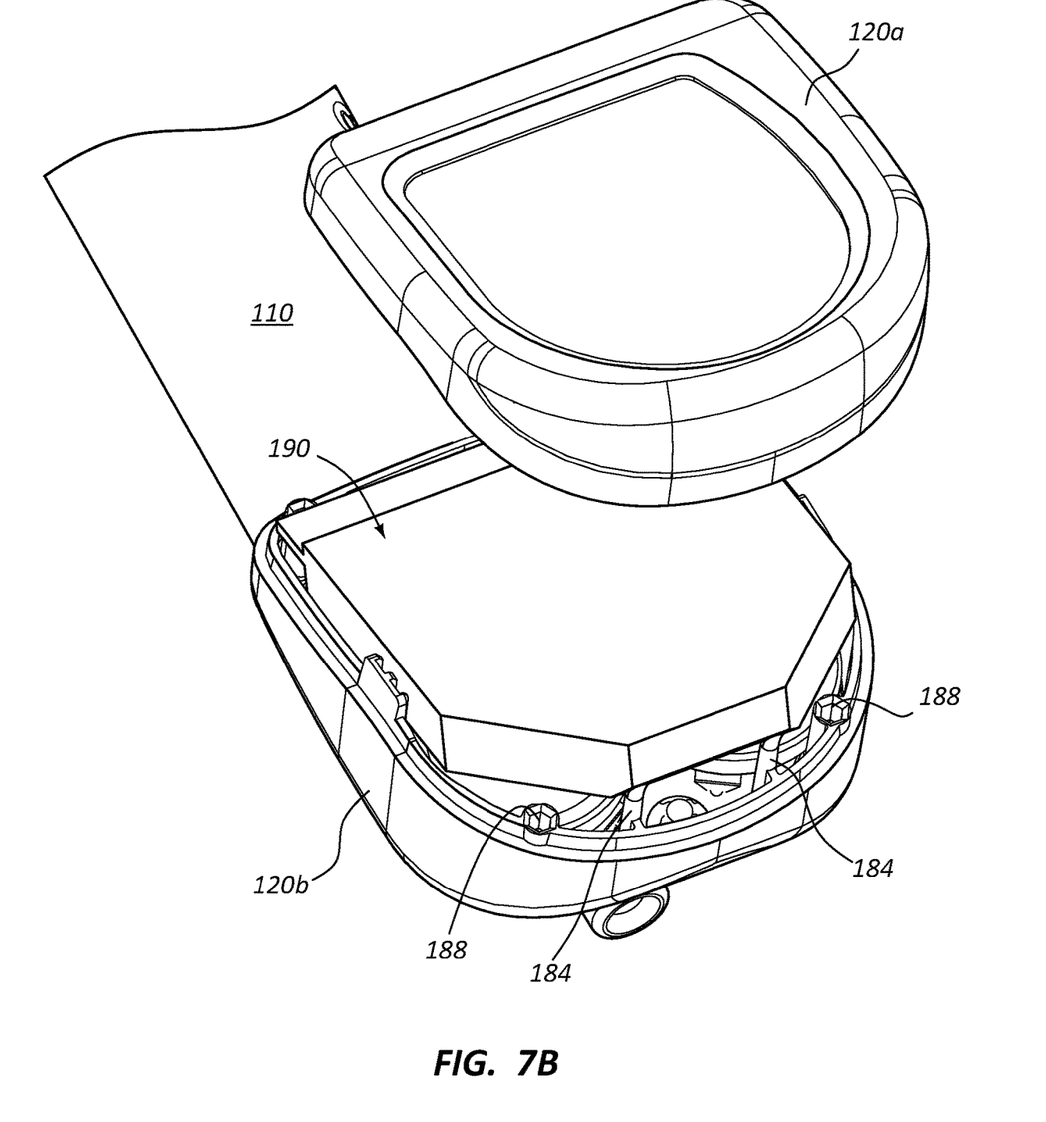
FIG. 7B is another perspective view of a portion of the inflation device of FIG. 1 in the partially assembled configuration of FIG. 7A.

FIGS. 7A and 7B provide alternative perspective views of a distal end of the inflation device 100 in a partially assembled configuration. More particularly, these figures depict the coupling of a display screen 190 (e.g., a liquid crystal display screen) and an upper portion of the housing 120a with other components of the inflation device 100.

More particularly, as depicted in FIGS. 7A and 7B, the display screen 190 may be placed over and electrically coupled with the circuit board 170 such that the display screen 190 is supported by a plurality of resilient pins 184 that are coupled to the lower portion of the housing 120b. The depicted embodiment includes a first set of two distal resilient pins 184 and a second set of two proximal resilient pins 184. The resilient pins 184 are configured to contact one or more outer surfaces of the display screen 190 adjacent bottom edges of the display screen 190. In some embodiments, the display screen 190 includes one or more angled surfaces that are configured for interaction with the resilient pins 184.

As mentioned above in connection with FIGS. 5A and 5B, the resilient pins 184 may include a ledge 186 and an angled portion 185 adjacent the tips of the resilient pins 184. In other embodiments, the resilient pins may lack a ledge. The angled portion 185 of each resilient pin 184 may be configured to deflect outward (i.e., away from the display screen 190) as a downward force is applied to the display screen 190. In other words, as increasing downward force is applied to the display screen 190, the resilient pins 184 may deflect outward, thereby allowing downward displacement of the display screen 190 relative to the lower portion of the housing 120b. The ledges 186 of the resilient pins 184 may limit the extent to which the display screen 190 may be displaced toward the lower portion of the housing 120b. The inflation device 100 may be configured to accommodate displays screens 190 of varied dimensions due to the deflection capabilities of the resilient pins 184. Stated differently, the resilient pins 184 may deflect to a greater extent when a relatively thick display screen 190 is disposed between the resilient pins 184 and the upper portion of the housing 120a than when a relatively thin display screen 190 is disposed between the resilient pins 184 and the upper portion of the housing 120a. In this manner, the resilient pins 184 may, within a range, take up tolerances relating to the thickness or other dimension of the display screen 190.

Downward force may be applied to the display screen 190 by an upper portion of the housing 120a. Stated differently, as the upper portion of the housing 120a is coupled to the lower portion of the housing 120b (e.g., via coupling elements 188), the upper portion of the housing 120a may press against the display screen 190, causing both (1) downward displacement of the display screen 190 relative to the lower portion of the housing 120b and (2) outward deflection of the resilient pins 184. The upper portion of the housing 120a and the lower portion of the housing 120b may be coupled together via a snap-fit connection. By coupling the upper portion of the housing 120a to the lower portion of the housing 120b in this manner, the housing 120a, 120b may enclose a plurality of components, such as the circuit board 170, the power source 180, and the display screen 190. In other words, the circuit board 170, the power source 180, and display screen 190 may each be disposed within the housing 120a, 120b.

In some embodiments, the resilient pins 184 are sized such that the display screen 190 is tilted. For example, the resilient pins 184 disposed adjacent the distal end of the lower portion of the housing 120b may be of greater length than the resilient pins 184 that are disposed adjacent the proximal end of the lower portion of the housing 120b, such that the proximal end of the display screen 190 is disposed at a position that is lower than the position of the distal end of the display screen 190. Tilting of the display screen 190 in this manner may place the display screen 190 in a position that allows a practitioner to monitor the pressure readout and/or other information on the display screen 190 better than if the display screen 190 were parallel to the longitudinal axis of the syringe body 110.

With reference to FIGS. 1-7B, when the inflation device 100 is in an assembled state, the display screen 190 may be in electrical communication with the circuit board 170 and the pressure transducer 140. For example, a signal from the pressure transducer 140 that is representative of the pressure within the fluid reservoir 112 of the syringe body 110 may be relayed to the electrical contacts 144 of the base plate 142 via one or more electrical conduits. The signal may then be further relayed from the electrical contacts 144 of the base plate 142 to the circuit board 170 via a solderless connection (e.g., via the elastomeric connector 150). After the signal has been processed by the circuit board 170, the circuit board 170 may send or relay a signal to a display screen 190. The display screen 190 may then provide a visible readout that is representative of the pressure within the fluid reservoir 112 of the syringe body 110.

With further reference to FIGS. 1-7B, inflation devices, such as inflation device 100, may be manufactured by a process that includes one or more of the following steps: obtaining a syringe body 110 that is coupled to an adaptor 130, inserting the adaptor 130 into an opening 126 of a lower portion of a housing 120b, and/or locking the adaptor 130 to the lower portion of the housing 120b.

In some embodiments, locking the adaptor 130 to the lower portion of the housing 120b includes depressing at least a portion of a lock 154 such that the lock 154 engages with the adaptor 130 to prevent movement of the adaptor 130 relative to the lower portion of the housing 120b.

In some embodiments, the method of manufacturing an inflation device 100 may include coupling an upper portion of the housing 120a to the lower portion of the housing 120b such that the housing 120 encloses a circuit board 170 and a display screen 190. In such embodiments, coupling the upper portion of the housing 120a to the lower portion of the housing 120b may exert a force on the display screen 190 that causes deflection of one or more resilient pins 184 that both support the display screen 190 and are coupled to the housing 120.

In some embodiments, the display screen 190 is disposed between the upper portion of the housing 120a and the one or more resilient pins 184 such that a downward force applied to the display screen 190 via the upper portion of the housing 120a causes both (1) downward displacement of the display screen 190 relative to the lower portion of the housing 120b and (2) outward deflection of the one or more resilient pins 184.

In some embodiments, inserting the adaptor 130 into the opening 126 of the lower portion of the housing 120b causes deflection of at least a portion of the lock 154.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

The invention claimed is:

1. A syringe assembly comprising:
an elongate syringe barrel defining a fluid reservoir;
a housing that is coupled to the elongate syringe barrel via a snap-fit connection;
a pressure transducer;
an aperture that extends through a wall of the elongate syringe barrel such that the fluid reservoir of the elongate syringe barrel is in fluid communication with the pressure transducer,
wherein the snap-fit connection comprises:
an adaptor that is coupled to the elongate syringe barrel, the adaptor comprising a plurality of flanges, each flange including a lower surface extending parallel to a bottom surface of the adaptor,
wherein each lower surface is in overlapping contact with an upper surface of a lower portion of the housing, and
wherein the upper surface is an inside surface within a cavity of the housing; and
a lock that is coupled to the housing, the lock preventing movement of the adaptor relative to the housing.

2. The syringe assembly of claim 1, further comprising a circuit board and a display screen, wherein the circuit board and the display screen are each disposed within the housing.

3. The syringe assembly of claim 2, wherein the pressure transducer is disposed between the adaptor and the lock.

4. The syringe assembly of claim 3, wherein the pressure transducer, circuit board, and display screen are configured for electrical communication with one another.

5. The syringe assembly of claim 1, wherein the lock is configured to engage with the adaptor to prevent movement of the adaptor relative to the housing after the lock has been depressed.

6. The syringe assembly of claim 1, wherein the lock comprises a first portion for coupling to the housing and a second portion that is configured to deflect upward as the adaptor is inserted into the housing.

7. The syringe assembly of claim 6, wherein the pressure transducer is in electrical communication with the circuit board via a solderless electrical connection.

8. The syringe assembly of claim 6, wherein the pressure transducer is in electrical communication with the circuit board via an elastomeric connector.

9. The syringe assembly of claim 8, wherein the elastomeric connector extends through the lock.

10. The syringe assembly of claim 2, wherein the display screen is supported by a plurality of resilient pins that are coupled to the housing, wherein the plurality of resilient pins are configured to deflect due to one or more forces applied to the display screen.

11. The syringe assembly of claim 10, wherein the plurality of resilient pins are vertically oriented when undeflected, and the resilient pins are configured to deflect in a generally outward direction due to one or more forces applied to the display screen.

12. The syringe assembly of claim 1, wherein the aperture has a radius of less than or equal to 0.8 mm in length.

13. The syringe assembly of claim 12, wherein the aperture has a radius of less than or equal to 0.6 mm in length.

14. The syringe assembly of claim 1, wherein at least one flange is in overlapping contact with an angled portion of the upper surface.

* * * * *